United States Patent
Kabiri et al.

(10) Patent No.: US 10,780,159 B2
(45) Date of Patent: Sep. 22, 2020

(54) CHIMERIC PEPTIDES AGAINST HTLV-1

(71) Applicants: Mona Kabiri, Mashhad (IR); Mohsen Tafaghodi Piadeh Gheibi, Mashhad (IR); Mojtaba Sankian, Mashhad (IR)

(72) Inventors: Mona Kabiri, Mashhad (IR); Mohsen Tafaghodi Piadeh Gheibi, Mashhad (IR); Mojtaba Sankian, Mashhad (IR)

( * ) Notice: Subject to any disclaimer, the term of this patent is extended or adjusted under 35 U.S.C. 154(b) by 214 days.

(21) Appl. No.: 15/846,043

(22) Filed: Dec. 18, 2017

(65) Prior Publication Data

US 2018/0099042 A1    Apr. 12, 2018

Related U.S. Application Data

(60) Provisional application No. 62/435,873, filed on Dec. 19, 2016.

(51) Int. Cl.
| | | |
|---|---|---|
| *A61K 39/21* | (2006.01) | |
| *A61K 39/12* | (2006.01) | |
| *C07K 14/005* | (2006.01) | |
| *C12N 7/00* | (2006.01) | |
| *A61K 39/00* | (2006.01) | |

(52) U.S. Cl.
CPC ............ *A61K 39/21* (2013.01); *A61K 39/12* (2013.01); *C07K 14/005* (2013.01); *C12N 7/00* (2013.01); *A61K 2039/54* (2013.01); *A61K 2039/543* (2013.01); *A61K 2039/545* (2013.01); *A61K 2039/57* (2013.01); *A61K 2039/575* (2013.01); *C07K 2319/40* (2013.01); *C12N 2740/14022* (2013.01); *C12N 2740/14034* (2013.01); *C12N 2740/14051* (2013.01); *C12N 2740/14071* (2013.01)

(58) Field of Classification Search
None
See application file for complete search history.

(56) References Cited

U.S. PATENT DOCUMENTS

| | | |
|---|---|---|
| 5,066,579 A | 11/1991 | Reyes |
| 5,670,311 A | 9/1997 | Vahlne et al. |
| 2010/0112071 A1 | 5/2010 | Kaumaya |

FOREIGN PATENT DOCUMENTS

| | | |
|---|---|---|
| EP | 1616950 A4 | 1/2007 |

OTHER PUBLICATIONS

Marin et al. "Chimeric Synthetic Peptides Containing Two Immunodominant Epitopes from the Envelope gp46 and the Transmembrane gp21 Glycoproteins of HTLV-I Virus", 2001, BBRC; 289:1-6.*
Of Lal, RB "Delineation of Immunodominant Epitopes of Human T-Lymphotropic Virus Types I and II and Their Usefulness in Developing Serologic Assays for Detection of Antibodies to HTLV-I and HTLV-II", 1996; 13LS170-178.*
Ratto-Kim et al. Heterologous Prime-Boost Regimens Using rAd35 and rMVA Vectors Elicit Stronger Cellular Immune Responses to HIV Proteins Than Homologous Regimens, PlosOne, 2012, 7(9): e45840.*
Aguilar MI. 2004, HPLC of Peptides and Proteins. In: Aguilar MI. (eds) HPLC of Peptides and Proteins. Methods in Molecular Biology™, vol. 251. Springer, Totowa, NJ., pp. 3-8.*
Zhang et al. "Effect of Vaccine Administration Modality on Immunogenicity and Efficacy", Expert Rev Vaccines. 2015; 14(11): 1509-1523.*
Zarnagh et al., Iran J. Allergy Asthma Immunol., Aug. 2015, 14(4):427-436. (Year: 2015).*
Pique et al., J. Virology, 1996, 70(8):4919-4926. (Year: 1996).*
Chen et al., Advanced Drug Delivery Reviews, 2013, 65:1357-1369. (Year: 2013).*
Arai et al., Protein Engineering, 2001, 14(5):529-532. (Year: 2001).*
UniProtKB/Swiss-Prot: Accession P23064.1, Nov. 1, 1991. (Year: 1991).*
UniProtKB/Swiss-Prot: Accession P03345.3, Jan. 23, 2007. (Year: 2007).*
Kazanji, M., et al., Chimeric peptide vaccine composed of B-and T-cell epitopes of human T-cell leukemia virus type 1 induces humoral and cellular immune responses and reduces the proviral load in immunized squirrel monkeys (*Saimiri sciureus*), Journal of general virology, 2006. vol. 87(5): pp. 1331-1337.
Sundaram, R., et al., A novel multivalent human CTL peptide construct elicits robust cellular immune responses in HLA-A? 0201 transgenic mice: implications for HTLV-1 vaccine design, Vaccine, 2003. vol. 21(21): pp. 2767-2781.
Sundaram, R., et al., De novo design of peptide immunogens that mimic the coiled coil region of human T-cell leukemia virus type-1 glycoprotein 21 transmembrane subunit for induction of native protein reactive neutralizing antibodies. Journal of Biological Chemistry, 2004. vol. 279(23): pp. 24141-24151.

(Continued)

*Primary Examiner* — Stacy B Chen
(74) *Attorney, Agent, or Firm* — Bajwa IP Law Firm; Haris Zaheer Bajwa

(57) ABSTRACT

A method of immunizing against HTLV-1 is disclosed. The method may include preparing a DNA sequence corresponding to a chimeric peptide which may have immunogenic epitopes of HTLV-1. These epitopes can include a Tax epitope, a gp21 epitope, a gp46 epitope, and/or a gag epitope. The method also includes production of the chimeric peptide using the DNA sequence and purifying the produced chimeric peptide. The purified chimeric peptide can be employed for immunization against HTLV-1.

10 Claims, 14 Drawing Sheets

Specification includes a Sequence Listing.

(56) References Cited

OTHER PUBLICATIONS

Lairmore, M.D., et al., Human T-lymphotropic virus type 1 peptides in chimeric and multivalent constructs with promiscuous T-cell epitopes enhance immunogenicity and overcome genetic restriction. Journal of virology, 1995. vol. 69(10): pp. 6077-6089.

Baba, E., et al., Multiple neutralizing B-cell epitopes of human T-cell leukemia virus type 1 (HTLV-1) identified by human monoclonal antibodies. A basis for the design of an HTLV-1 peptide vaccine, The Journal of Immunology, 1993. vol. 151(2): Abstract.

* cited by examiner

```
┌─────────────────────────────────────────────┐
│ Preparing a DNA sequence of a chimeric peptide │── 101
│   with Tax, gp21, gp46, and gag epitopes    │
└─────────────────────────────────────────────┘
                      │
                      ▼
┌─────────────────────────────────────────────┐
│  Producing the chimeric peptide using the DNA │── 102
│      sequence of the chimeric peptide        │
└─────────────────────────────────────────────┘
                      │
                      ▼
┌─────────────────────────────────────────────┐
│  Purifying the produced chimeric peptide to form a │── 103
│           purified chimeric peptide          │
└─────────────────────────────────────────────┘
                      │
                      ▼
┌─────────────────────────────────────────────┐
│ Immunizing against HTLV-1 through administration │── 104
│      of the purified chimeric peptide        │
└─────────────────────────────────────────────┘
```

CHIMERIC PEPTIDES AGAINST HTLV-1

CROSS-REFERENCE TO RELATED APPLICATION

This application claims the benefit of priority from pending U.S. Provisional Patent Application Ser. No. 62/435,873, filed on Dec. 19, 2016, and entitled "CHIMERIC PEPTIDES FROM HTLV-1," which is incorporated herein by reference in its entirety.

SPONSORSHIP STATEMENT

This application has been sponsored by Iran Patent Center, which does not have any rights in this application.

TECHNICAL FIELD

The present disclosure generally relates to peptides vaccines, and particularly to chimeric peptides against human T-lymphotropic virus type 1 (HTLV-1) for preventing HTLV-1 associated diseases. The present disclosure further relates to a method for immunization against HTLV-1.

BACKGROUND

The human T-lymphotropic virus type 1 (HTLV-1) is a group of human retroviruses which causes a type of cancer known as adult T-cell leukemia/lymphoma. In addition, the HTLV-1 can cause HTLV-1 associated myelopathy/tropical spastic paraparesis (HAM/TSP), a type of demyelinating disease. Therefore, production of a vaccine for immunization against HTLV-1 has considerable importance.

Conventional vaccines for prevention of HTLV-1 infections are produced from dead pathogens, attenuated pathogens, inactivated toxins, and recombinant subunits. However, the presence of immunologically redundant components or biological impurities in conventional vaccines also causes significant health problems. The development of synthetic peptide vaccines offers an alternative treatment option that is believed to overcome the disadvantages associated with conventional vaccines.

For example, peptide vaccines are understood to be intrinsically safer and more efficient than conventional vaccines. Moreover, peptide vaccines are capable of targeting relevant immunogenic epitopes. In addition, the use of peptide vaccines avoids immune evasion, as well as unwanted side effects such as autoimmunity. However, developing an efficient peptide vaccine is associated with many challenges, including the difficulty of overcoming low intrinsic immunogenicity of each epitope.

Therefore, there is a need in the art to provide peptide vaccines against HTLV-1 that can effectively stimulate the immune system without side effects, and raise immunization levels against the HTLV-1 for prevention of HTLV-1 associated diseases.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, a method for immunizing against HTLV-1 is disclosed. The method includes preparing a DNA sequence, where the DNA sequence encodes a chimeric peptide with immunogenic epitopes including a Tax epitope, a gp21 epitope, a gp46 epitope, and a gag epitope. The method also includes producing the chimeric peptide using the DNA sequence, purifying the produced chimeric peptide, and immunizing against HTLV-1 using the purified chimeric peptide.

The above general aspect may include one or more of the following features. In one example, the immunogenic epitopes are connected together with a linker. The linker includes a flexible linker, a helical linker, or combinations thereof The DNA sequence corresponding to the chimeric peptide with the flexible linkers is set forth in SEQ ID No. 1. The chimeric peptide with the flexible linkers has an amino acid sequence as set forth in SEQ ID No. 2.

The above general aspect may include one or more of the following features. In one example, the immunogenic epitopes are connected together sequentially with a linker, where the linker can include a flexible linker, a helical linker, or combinations thereof. In another example, the DNA sequence corresponding to the chimeric peptide with the flexible linkers is set forth in SEQ ID No. 1. In some implementations, the chimeric peptide with the flexible linkers has an amino acid sequence as set forth in SEQ ID No. 2. In one implementation, the DNA sequence corresponding to the chimeric peptide with the helical linkers is set forth in SEQ ID No. 3. In another case, the chimeric peptide with the helical linkers has an amino acid sequence as set forth in SEQ ID No. 4. In one other example, the flexible linker has a nucleotide sequence as set forth in SEQ ID No. 5. In some implementations, the helical linker has a nucleotide sequence as set forth in SEQ ID No. 6. Furthermore, in some implementations, preparing the DNA sequence further includes designing the DNA sequence and synthesizing the designed DNA sequence. In some cases, producing the chimeric peptide using the DNA sequence further includes preparing a recombinant vector including the DNA sequence, amplifying the recombinant vector, thereby obtaining a plurality of recombinant vectors, and expressing the chimeric peptide through cloning of the plurality of recombinant vectors in a host organism. As one example, a chromatographic technique is employed in the purification of the produced chimeric peptide, where the chromatographic technique includes affinity chromatography, immobilized metal ion affinity chromatography (IMAC), ion exchange chromatography (IEXC), gel filtration chromatography, hydrophobic interaction chromatography (HIC), or combinations thereof. In another example, the method of immunizing against HTLV-1 further includes administration of the chimeric peptide to a person, where the administration of the chimeric peptide occurs through a subcutaneous injection (SC), a nasal route, intramuscular injection (IM), intravenous route (IV), or combinations thereof. In some implementations, immunizing against HTLV-1 further includes administration of the chimeric peptide at an amount ranging between approximately 10 μg and 30 μg.

In another general aspect, a chimeric peptide for inducing an immune response against human T-lymphotropic virus-1 (HTLV-1) is disclosed. The chimeric peptide includes a plurality of immunogenic epitopes of HTLV-1. The epitopes further include a Tax epitope, a gp21 epitope, a gp46 epitope, and a gag epitope. In addition, the immunogenic epitopes are connected together sequentially with a linker.

The above general aspect may include one or more of the following features. In one example, the linker can include a flexible linker, a helical linker, or combinations thereof. In another example, chimeric peptide with the flexible linkers has an amino acid sequence as set forth in SEQ ID No. 2. In some implementations, the chimeric peptide with the flexible linkers has 274 amino acid residues. In another implementation, the chimeric peptide with the helical linkers has an amino acid sequence as set forth in SEQ ID No. 4. In some cases, the chimeric peptide with the helical linkers has 317 amino acid residues. In another example, a DNA sequence corresponding to the chimeric peptide with the flexible linkers is set forth in SEQ ID No. 1.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1 depicts a method for immunizing against HTLV-1, according to an implementation of the present disclosure;

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

One approach used in the development of peptide vaccines against HTLV-1 is producing a single-epitope peptide vaccine. However, use of a single epitope or minimal immunogenic epitopes for immunizing against HTLV-1 may lead to inefficient immune responses and may further prevent the induction of an appropriate immune response. Because single-epitope peptide vaccines are inefficient for inducing proper immune responses against HTLV-1, alternatives are needed. The present application describes a novel fusion of multiple immunogenic epitopes of HTLV-1 into a chimeric peptide vaccine that may provide a comprehensive immunity. The associated chimeric peptide may also overcome the shortcomings of single-epitope peptide vaccines.

The following disclosure presents a chimeric peptide and a method for immunizing against HTLV-1 through administration of a chimeric peptide as a vaccine. The chimeric peptide may benefit from inclusion of multiple immunogenic epitopes of HTLV-1. In one implementation, a chimeric peptide including immunogenic epitopes of HTLV-1 is disclosed. As one example, a chimeric peptide including a Tax epitope, a gp21 epitope, a gp46 epitope, and a gag epitope is disclosed. In some implementations, the immunogenic epitopes may be connected together sequentially with a linker.

As noted above, the administration of the chimeric peptide as a vaccine may induce an effective immune response against HTLV-1. In some implementations this induced immune response may be mediated by distinct subsets of helper T cells, such as T-helper 1 (Th1) and T-helper (Th2). Th1 and Th2 cells are effective against different viruses, including HTLV-1. Thus, the disclosed chimeric peptide may be used for immunizing against HTLV-1 and thereby preventing associated diseases, such as adult T-cell leukemia/lymphoma, HTLV-I associated myelopathy (HAM), and HTLV-1-associated myelopathy/tropical spastic paraparesis (HAM/TSP).

Referring now to FIG. 1, an overview of a method 100 for immunization against HTLV-1 is provided in a flow chart in order to introduce the reader to one implementation of the present disclosure. As shown in FIG. 1, the method 100 includes a first step 101 of preparing a DNA sequence which encodes a chimeric peptide with a Tax epitope, a gp21 epitope, a gp46 epitope, and a gag epitope. A second step 102 includes producing the chimeric peptide using the DNA sequence, followed by a third step 103 of purifying the produced chimeric peptide. A fourth step 104 involves immunizing against HTLV-1 using the purified chimeric peptide. Further details regarding the method are provided below.

As presented in FIG. 1, the first step 101 in a method of immunization against HTLV-1 may include preparing a DNA sequence which encodes the chimeric peptide. In different implementations, the chimeric peptide may include multiple immunogenic epitopes of HTLV-1. For example, in some implementations, a Tax epitope, a gp21 epitope, a gp46 epitope, and/or a gag epitope, may be connected sequentially together via a linker. In some implementations, the DNA sequence may include nucleotide sequences of multiple immunogenic epitopes of HTLV-1. For example, in one implementation, the DNA sequence can include nucleotide sequences of a Tax epitope, a gp21 epitope, a gp46 epitope, and/or a gag epitope. Moreover, in some implementations, the DNA sequence may include a nucleotide sequence(s) of a linker that can connect the nucleotide sequences of the immunogenic epitopes sequentially.

Furthermore, during first step 101, the DNA sequence may be prepared via a process including designing the DNA sequence, and synthesizing the designed DNA sequence in some implementations. In some cases, the DNA sequence may be designed utilizing bioinformatics software. In one implementation, the spatial arrangement and three-dimensional structure of the immunogenic epitopes of the chimeric peptide may be designed to provide a configuration suitable for proper folding of the chimeric peptide. In some implementations, after designing the DNA sequence, the designed DNA sequence may be synthesized using an artificial DNA synthesis process which includes a chemical synthesis of DNA fragments.

Figure 2A:
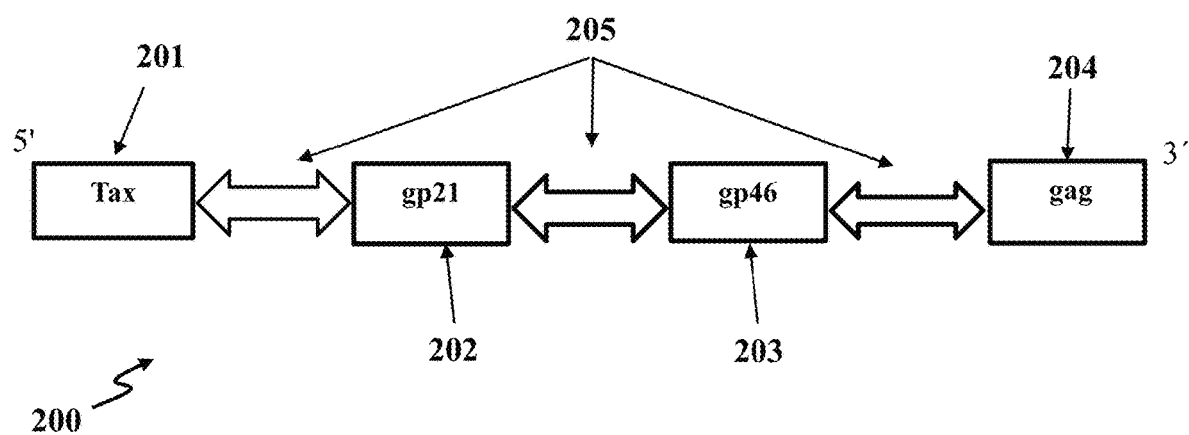
FIG. 2A is a schematic illustration of a DNA sequence which encodes a chimeric peptide, according to an implementation of the present disclosure.

Referring next to FIG. 2A, a schematic illustration of a DNA sequence 200 of a chimeric peptide is depicted, according to an implementation of the present disclosure. As shown in the implementation of FIG. 2A, the DNA sequence 200 of the chimeric peptide may include nucleotide sequences of a Tax epitope 201, a gp21 epitope 202, a gp46 epitope 203, and a gag epitope 204. These may be connected together sequentially with a linker 205. The linker 205 may include a flexible linker, a helical linker, or combinations thereof In some implementations, SEQ ID No. 1 represents the designed DNA sequence 200 of the chimeric peptide with the flexible linkers. In another implementation, SEQ ID No. 3 is the designed DNA sequence 200 of the chimeric peptide with the flexible linkers. According to some implementations, the flexible linker may have a nucleotide sequence as set forth in SEQ ID No. 5. In one implementation, the helical linker may include a nucleotide sequence as set forth in SEQ ID No. 6.

Figure 2B:
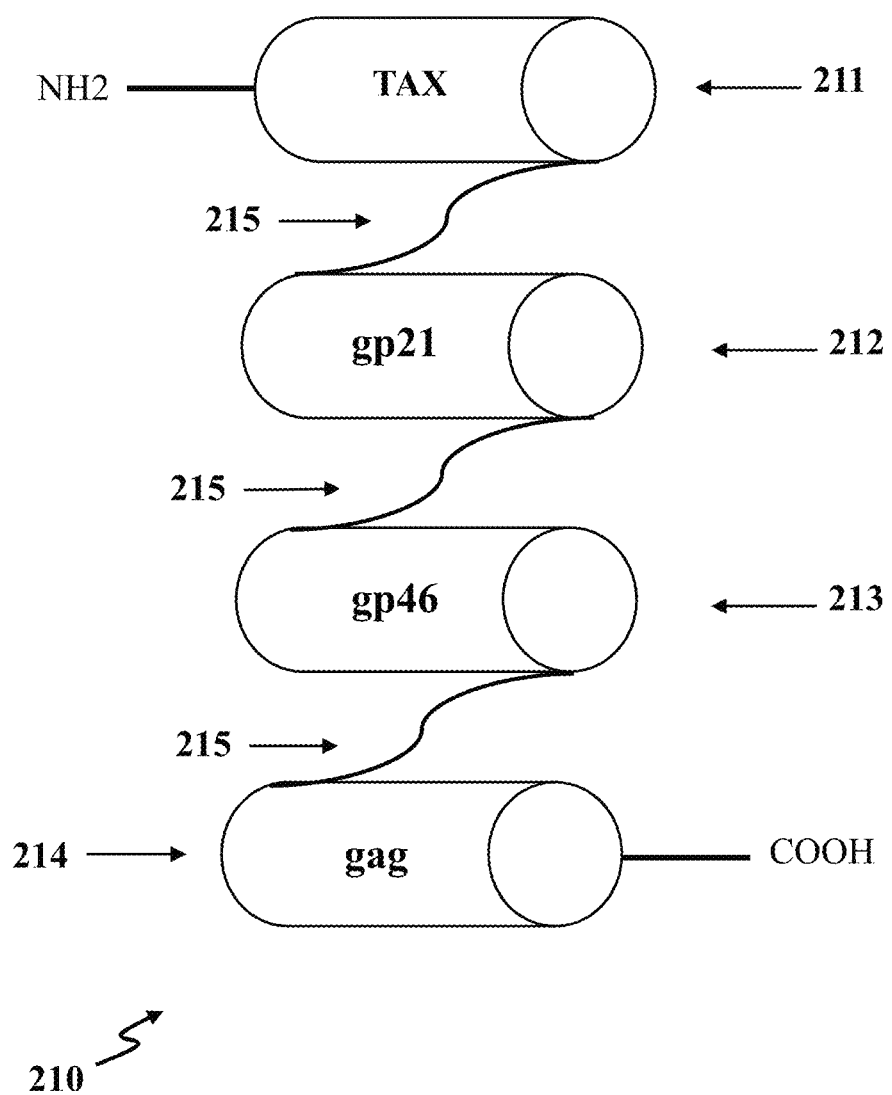
FIG. 2B is a schematic illustration of a chimeric peptide, according to an implementation of the present disclosure.

Another example of a chimeric peptide 210 is provided in the schematic illustration of FIG. 2B. The chimeric peptide 210 may be encoded from the DNA sequence 200, according to an implementation of the present disclosure. In one implementation, the chimeric peptide 210 may include a Tax epitope 211, a gp21 epitope 212, a gp46 epitope 213, and a gag epitope 214, which may be connected sequentially with a linker 215. The linker 215 may include a flexible linker, a helical linker, or combinations thereof Referring to both FIGS. 2A and 2B, in some implementations, the Tax epitope 211 may be encoded from the nucleotide sequence of the Tax epitope 201. Furthermore, in some implementations, the gp21 epitope 212 may be encoded from the nucleotide sequence of the gp21 epitope 202. in one implementation, the gp46 epitope 213 may be encoded from the nucleotide sequence of the gp46 epitope 203. In addition, in some implementations, the gag epitope 214 may be encoded from the nucleotide sequence of the gag epitope 204. Moreover, in one implementation, the linker 215 may be encoded from the nucleotide sequence of the linker 205.

In different implementations, the chimeric peptide 210 with the flexible linkers may have an amino acid sequence as set forth in SEQ ID No. 2. In one implementation, the chimeric peptide 210 with the flexible linkers may include about 274 amino acid residues. Moreover, the chimeric peptide 210 with the flexible linkers may have a molecular weight ranging between about 25 and about 55 kiloDalton (kDa).

In another implementation, the chimeric peptide 210 with the helical linkers may have an amino acid sequence as set forth in SEQ ID No. 4. The chimeric peptide 210 with the helical linkers may have a molecular weight ranging between about 30 and about 60 kiloDalton (kDa). The chimeric peptide 210 with the helical linkers may include about 317 amino acid residues.

Referring again to the method 100 of FIG. 1, in some implementations, second step 102 of method 100 may include producing the chimeric peptide using the DNA sequence. In different implementations, producing the chimeric peptide may include preparing a recombinant vector including the DNA sequence, amplifying the recombinant vector to obtain a plurality of recombinant vector, and/or expressing the chimeric peptide through cloning of the plurality of recombinant vector into a host organism.

At first, in order to prepare a recombinant vector including the DNA sequence, the synthesized DNA sequence may be inserted into a vector to prepare a recombinant vector including the DNA sequence. In some implementations, the vector may be selected from a plasmid, a bacteriophage, a cosmid, a bacterial artificial chromosome (BAC), a yeast artificial chromosome (YAC), human artificial chromosome, or combinations thereof Furthermore, in one implementation, preparation of the recombinant vector may include inserting the DNA sequence into a vector. The insertion may utilize restriction enzymes in some cases, though in other cases the insertion may be accomplished without use of restriction enzymes. In non-restriction enzyme methods, inserting the DNA sequence may be done using a megaprimer method in some implementations.

In restriction-enzyme based methods, the vector may be cut using restriction enzymes to form two sticky ends in some implementations. Moreover, in one implementation, two sticky ends may be provided or formed at each end of DNA sequence by designing restriction sites at both sides of DNA sequence. Following this step, the DNA sequence may be inserted into the vector through ligation of the sticky ends of the DNA sequence to the sticky ends of the vector.

Once the DNA sequence has been inserted into the vector, the prepared recombinant vector which has the DNA sequence of the chimeric peptide may be amplified and a plurality of recombinant vector(s) may be obtained. In some implementations, amplification of the recombinant vector may include transforming the recombinant vector of the chimeric peptide to a bacterial host, and then performing a colony polymerase chain reaction (PCR).

In order to subsequently express the chimeric peptide in a host organism, the plurality of recombinant vectors including the DNA sequence may be transformed to a bacterial host, such as, for example, *Escherichia coli* (*E. coli*), though in other implementations other hosts may be used. As a result, the chimeric peptides may be expressed in the bacterial host during the bacterial growth in some implementations. In addition, expression of the chimeric peptide may be optimized, and expression confirmation may be done utilizing SDS-PAGE and western blot techniques in some implementations.

With respect to third step 103, according to an implementation, the produced chimeric peptide may be purified. Purification of the chimeric peptide may be performed through application of chromatographic techniques such as affinity chromatography, immobilized metal ion affinity chromatography (IMAC), ion exchange chromatography (IEXC), gel filtration chromatography, hydrophobic interaction chromatography, or combinations thereof In some implementations, while the chimeric peptides may be expressed in a form of inclusion bodies and their proper folding may be changed after the purification, the purified chimeric peptide may be refolded through a dialysis process. Finally, the purified samples of chimeric peptides may be confirmed by SDS-PAGE and western blot techniques.

Referring now to the fourth step 104, in different implementations, immunizing against HTLV-1 can involve administration of the purified chimeric peptide through a subcutaneous injection (SC), a nasal route, intramuscular injection (IM), and intravenous route (IV), or combinations thereof. Moreover, in some implementations, the chimeric peptide may be administered with a vaccine dosage of between about 10 μg and about 30 μg.

After administration of the chimeric peptide, the immune system of the patient or subject may be stimulated. This stimulation may induce an effective immune response against HTLV-1 for preventing HTLV-1 associated virus. In some cases, the induced immune response may be mediated by distinct subsets of helper T cells, such as T-helper 1 (Th1) and T-helper (Th2), which are protective cells against different viruses, including HTLV-1.

EXAMPLES

Example 1

Producing Chimeric Peptides Against HTLV-1

In Example 1, chimeric peptide vaccines were produced through the series of steps described herein. A first step included preparing a DNA sequence which encodes a chimeric peptide with Tax, gp21, gp46, and gag epitopes. A second step included producing the chimeric peptide using the DNA sequence. A third step involved purifying the produced chimeric peptide. The fourth step included immunizing against HTLV-1 using the purified chimeric peptide. Further details regarding this Example are provided below.

The DNA sequence encoding a chimeric peptide with Tax, gp21, gp46, and gag epitopes was prepared through a process that included designing the DNA sequence, and synthesizing the designed DNA sequence. The design of the DNA sequence utilized a bioinformatics software. The spatial arrangement and three-dimensional structure of epitopes were designed with a configuration suitable for proper folding of the chimeric peptide.

Referring back to FIG. 2, in this Example, the Tax epitope 201, the gp21 epitope 202, the gp46 epitope 203, and the gag epitope 204 along with the linkers 205 were applied in the design of the DNA sequence. SEQ ID No. 1 is the designed construction of the DNA sequence corresponding to the chimeric peptide with the flexible linkers. Moreover, SEQ ID No. 3 is the designed construction of the DNA sequence corresponding to the chimeric peptide with the helical linkers.

Following the design step, the designed DNA sequences of the chimeric peptides were synthesized using an artificial DNA synthesis process, which was a chemical synthesis of DNA fragments. In the next step, the synthesized DNA sequence was cloned into PET32b (+) as a plasmid vector.

Following the synthesis of the DNA sequences, the chimeric peptide was produced by a process involving three general steps. The first step involved preparing a recombinant PET32b (+) plasmid which includes the DNA sequence. The second step included amplification of the recombinant PET32b (+) plasmid including the DNA sequence. The third step included expressing the chimeric peptide through cloning the recombinant plasmid PET32b (+) into a bacterial host.

In order to prepare a recombinant plasmid PET32b (+) including the DNA sequence as identified in the first step, the synthesized DNA sequence was inserted into the PET32b (+) plasmid. This was accomplished by first cutting the PET32b (+) plasmids using Hind III and Xho I restriction enzymes to form sticky ends. Moreover, sticky ends of Hind III and Xho I were provided or available at ends of the DNA sequence through designing the restriction sites of the Hind III and Xho I enzymes at both sides of the DNA sequence.

The PET32b (+) plasmid and the DNA sequence, which both have sticky ends, were then purified using a gel extraction method. In order to prepare the recombinant PET32b (+) plasmid, the DNA sequence with two sticky ends was inserted into the PET32b (+) through ligation of the sticky ends of the DNA sequence to the sticky ends of the PET32b (+) plasmid vector.

The PET32b (+) plasmid vector was designed for high-level expression of the chimeric peptide, and this plasmid vector had a thioredoxin protein tag (Trx-Tag) sequence which was located downstream of the DNA sequence corresponding to the chimeric peptide. Therefore, the chimeric peptide which was expressed using the PET32b (+) plasmid vector had a Trx-tag at its end. The Trx-tag had a molecular weight of between about 18 kDa and about 25 kDa. The prepared recombinant PET32b (+) plasmid which had the DNA sequence was then amplified by using transformed recombinant PET32b (+) plasmids which included DNA sequence to a bacterial host, and then performing a colony polymerase chain reaction (PCR).

Confirmation of the recombinant PET32b (+) plasmids was accomplished by transforming the recombinant PET32b (+) plasmids into TOP10 competent *Escherichia coli* (*E. coli*) cells, and then performing a polymerase chain reaction (PCR) using T7 universal primers as well as by a DNA sequencing method. The T7 universal primers are PCR primers which bind to a sequence which is found in many plasmid vectors, including PET32b (+).

In order to express the chimeric peptide in a host organism, the amplified recombinant vector including the DNA sequence was transformed to a bacterial host, for example, in this case, *Escherichia coli* (strain B/BL21-DE3). As a result, the chimeric peptides were expressed in the bacterial host during the bacterial growth. Furthermore, expression of the chimeric peptide was optimized, and expression confirmation accomplished utilizing SDS-PAGE and western blot techniques.

In order to produce the chimeric peptide in a host organism using the DNA sequence, the DNA sequence was amplified using transforming the DNA sequence to a bacterial host, and then performing a colony polymerase chain reaction (colony PCR). The products of the colony PCR were then loaded on electrophoresis gel to determine the band that included the DNA sequence. A colony PCR was performed to screen and select the bacterial colonies which had the recombinant plasmid including the DNA sequence.

After screening, the recombinant plasmids of the selected colonies were extracted with a plasmid DNA extraction kit. The amplified recombinant plasmids were then transformed to an expression bacterial host, for example in this case, *Escherichia coli* (*E. coli*). Therefore, the chimeric peptides were expressed in the bacterial host during the bacterial growth.

In order to optimize the level of chimeric peptide expression, isopropyl β-D-1-thiogalactopyranoside (IPTG) inducer was used for inducing the chimeric peptide expression in the bacterial cells. The IPTG was added with a concentration of between about 0.6 mM and about 1 mM. The IPTG was added to the bacterial cells when the optical density of the bacterial cells at a wavelength of about 600 nm reached between 0.4 and 0.6.

Moreover, the bacterial cells were incubated with IPTG for a period of between about 16 hours and about 18 hours. The bacterial cells were centrifuged and the chimeric peptide extracted from the inclusion bodies. Following optimization of the chimeric peptide expression, the expression was confirmed by utilization of SDS-PAGE and western blot techniques.

The high expression level of the chimeric peptides in *E. coli* resulted in a protein aggregation which formed inclusion bodies. Moreover, the interactions between hydrophobic regions of protein caused the formation of inclusion bodies during the expression of the chimeric peptide in the *E. coli* host. Therefore, in order to obtain a soluble form of chimeric peptide for purification, the inclusion bodies were solubilized. In this case, the solubilization of the inclusion bodies was performed using urea and guanidine hydrochloride chaotropic agents.

In the next step, the produced chimeric peptides were purified. In the PET32b (+) plasmid vector, there was a histidine tag (His-tag) sequence after the DNA sequence of the chimeric peptide, and the chimeric peptide was expressed with a His-tag at its end. Due to the presence of the His-tag which was fused to the chimeric peptide, an affinity chromatography technique can be used for purifying the chimeric peptide. Thus, the chimeric peptides were purified using an immobilized metal ion affinity chromatography (IMAC) with a nickel nitrilotriacetic acid (Ni-NTA) chromatography column.

Refolding of the chimeric peptides was accomplished through a dialysis process. For the purpose of refolding, the chimeric peptide was refolded using about 50 mM of phosphate buffered saline solution (PBS) at pH of about 7.4 for overnight dialysis at 4° C. The PBS solution included 150 mM of NaCl, 20% of glycerol (volume/volume).

Figure 3A:
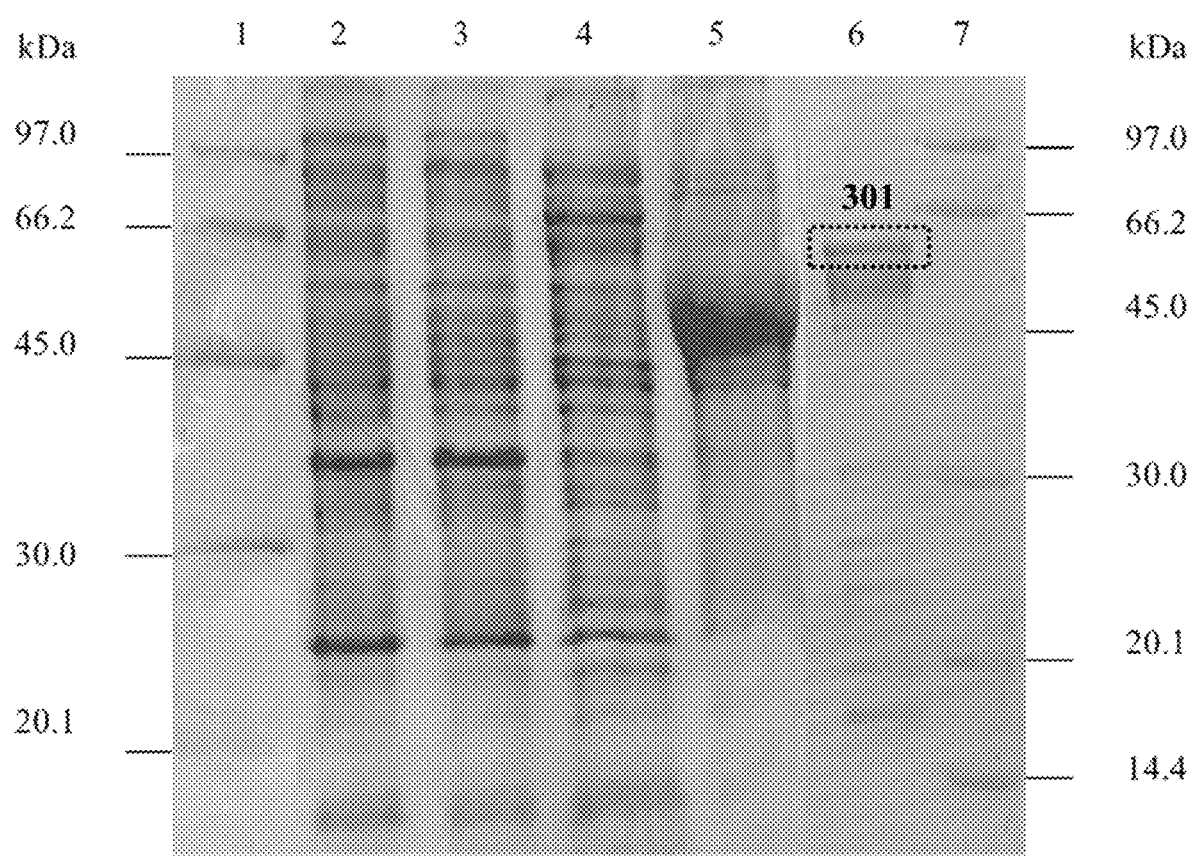
FIG. 3A illustrates a SDS-PAGE profile of a chimeric peptide with helical linkers, according to an implementation of the present disclosure.

In order to perform the SDS-PAGE technique, the chimeric peptides were fractionated on a 12.5% SDS-PAGE and became visible using a Coomassie blue staining. FIG. 3A illustrates an implementation of a SDS-PAGE profile of chimeric peptide with helical linkers which was expressed in *E. coli* BL21 (DE3), according to an implementation of the present disclosure.

Referring to FIG. 3A, lanes 1 and 7 are markers of protein molecular weight. Lane 2 is a BL21 (DE3) soluble fraction. Lane 3 is a BL21 (DE3) insoluble fraction. Lane 4 is a soluble fraction of the chimeric peptide with helical linkers. Lane 5 is an insoluble fraction of the chimeric peptide with helical linkers, and lane 6 is a purified soluble chimeric peptide with helical linkers. As shown in lane 6, the SDS-PAGE profile of the chimeric peptide with helical linkers revealed a protein band 301 with a molecular weight of about 59 kDa, which is equivalent to a summation of molecular weights of the chimeric peptide with helical linkers, about 34 kDa, and the Trx-tag, about 25 kDa.

Figure 3B:
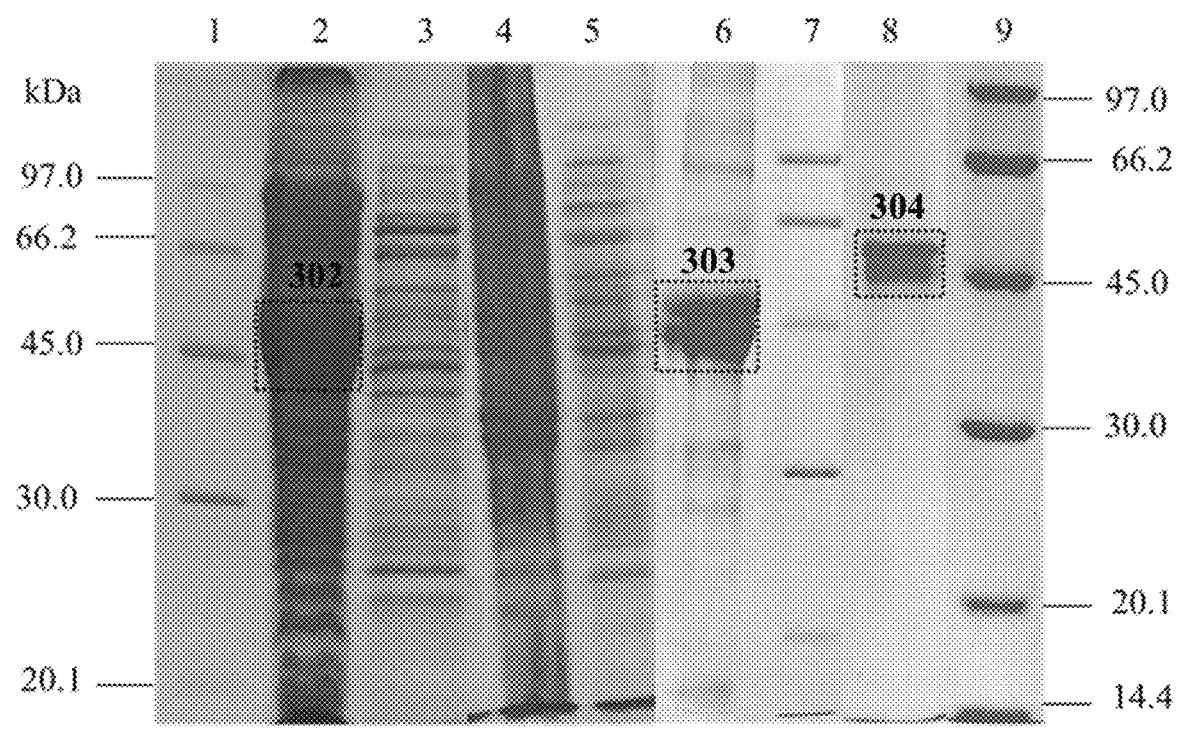
FIG. 3B illustrates a SDS-PAGE profile of a chimeric peptide with flexible linkers, according to an implementation of the present disclosure.

FIG. 3B illustrates an implementation of a SDS-PAGE profile of chimeric peptide with flexible linkers which is expressed in *E. coli* BL21 (DE3), according to an implementation of the present disclosure. Referring to FIG. 3B, lanes 1, 7, and 9 are markers of the protein molecular weight. Lane 2 is an insoluble fraction of the chimeric peptide with flexible linkers. Lane 3 is a soluble fraction of the chimeric peptide with flexible linkers. Lane 4 is a BL21 (DE3) insoluble fraction. Lane 5 is a BL21 (DE3) soluble fraction. Lane 6 is a purified soluble chimeric peptide with flexible linkers, and lane 8 is a highly purified soluble chimeric peptide with flexible linker.

As seen in FIG. 3B, the SDS-PAGE analysis of the chimeric with flexible linkers revealed an overexpression of a protein band 302. This reflects an overexpression of the chimeric peptide with flexible linkers at the predictable molecular weight of about 53 kDa, which is equivalent to summation of molecular weights of the chimeric peptide with flexible linkers, about 28 kDa, and the Trx-tag, about 25 kDa. In contrast, there are no overexpressed bands in the control group, as seen in lane 4 which is a BL21 (DE3) insoluble fraction. Moreover, the protein bands which are obtained after the dialysis process, protein band 303 and protein band 304, illustrate the high level expression of the soluble chimeric peptide with flexible linkers.

Referring to both FIGS. 3A and 3B, it can be seen that the expression level of the chimeric peptide with flexible linkers is higher than the expression level of the chimeric peptide with helical linkers. Therefore, the highest level of expression of the chimeric peptides can be achieved by insertion of flexible linkers between the immunogenic epitopes of the chimeric peptides.

In order to perform a western blot technique, the chimeric peptides were transmitted to a PVDF membrane, which was blocked with about 2% bovine serum albumin (BSA) overnight at 4° C. The chimeric peptides are identified by using a cross adsorbed anti His-tag antibody as primary antibodies, and a goat anti-rabbit antibody conjugated to horseradish peroxidase (HRP) as secondary antibodies. The western blot assay detects a single band of each of the chimeric peptides after the purification and the dialysis process.

Figure 4A:
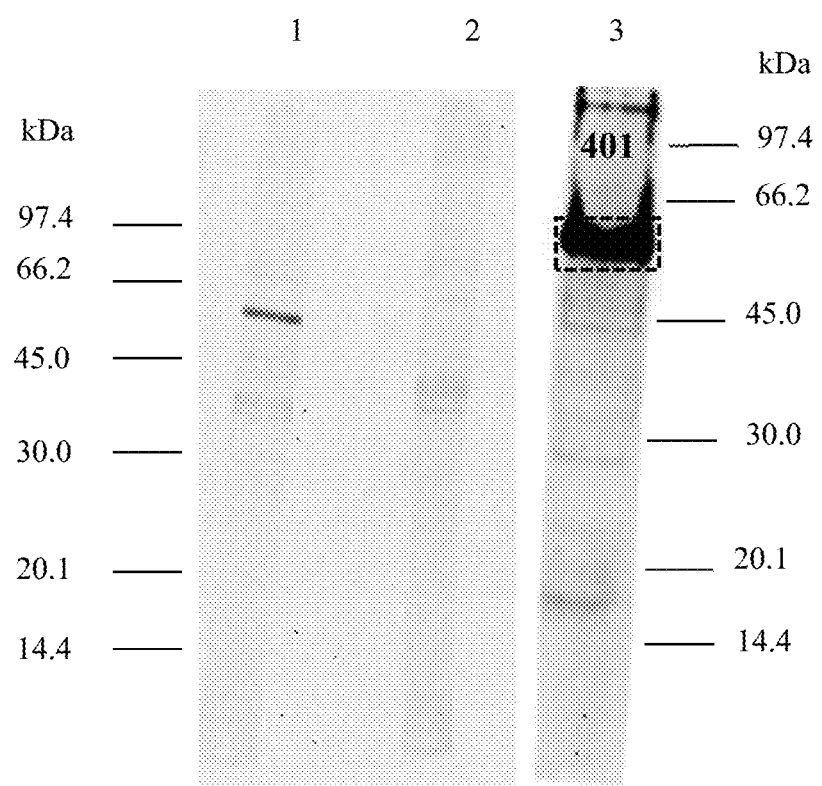
FIG. 4A illustrates a western blot analysis of a chimeric peptide with helical linkers, according to an implementation of the present disclosure.

Referring now to FIG. 4A, an implementation of a western blot analysis of chimeric peptide with helical linkers is illustrated, according to an implementation of the present disclosure. The western blot analysis was performed utilizing a cross adsorbed anti His-tag antibody as a primary antibody. The signal was detected using HRP-conjugated goat anti-rabbit secondary antibody and ECL reagents. In addition, the anti His-tag was diluted with PBS solution with a concentration of about 1:2000 (volume/volume). The signal was detected using a HRP-conjugated goat anti-rabbit secondary antibody. The HRP-conjugated goat anti-rabbit was diluted with PBS with a concentration of about 1:50000 (volume/volume).

In FIG. 4A, lane 1 is a chimeric peptide with helical linkers, lane 2 is a BL21 (DE3) control, and lane 3 is a purified soluble chimeric peptide with helical linkers. The western blot analysis of the chimeric peptide with helical linkers revealed a protein band 401.

Figure 4B:
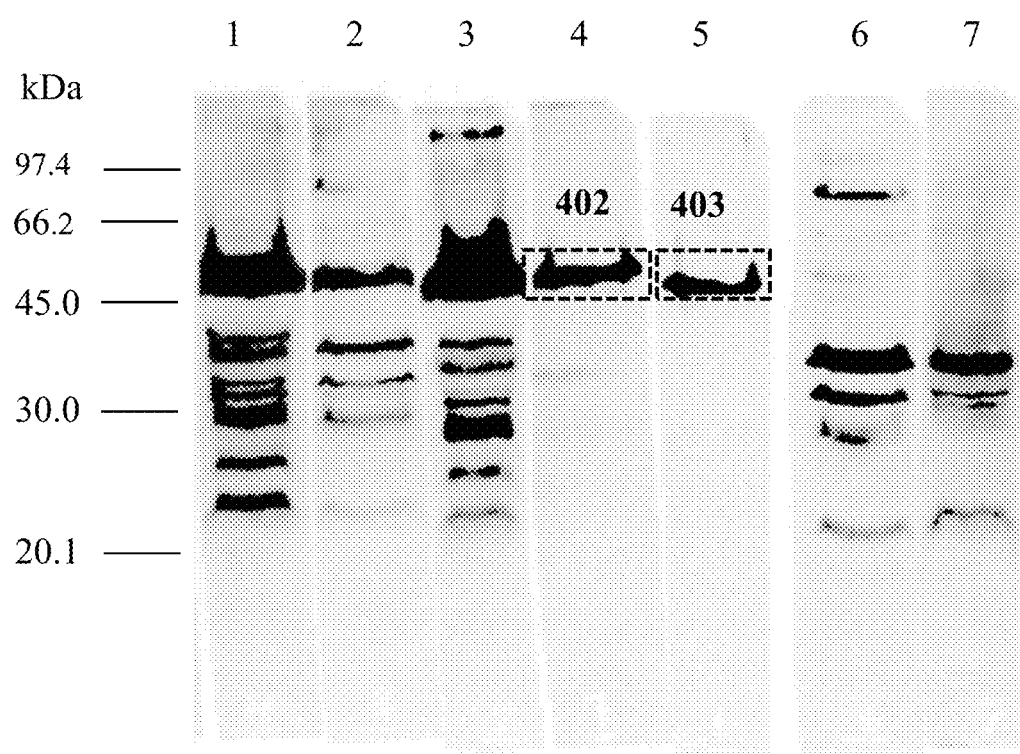
FIG. 4B illustrates a western blot analysis of a chimeric peptide with flexible linkers, according to an implementation of the present disclosure.

FIG. 4B illustrates a western blot analysis of chimeric peptide with flexible linkers, according to an implementation of the present disclosure. The high-level expression in *E. coli* BL21 (DE3) host by the insertion of flexible linker between chimeric epitope was analyzed by western blot. The chimeric peptides were evaluated by western blot using anti His-tag as a primary antibody. The signal was detected using a HRP-conjugated goat anti-rabbit secondary antibody. Furthermore, the anti His-tag was diluted with PBS solution with a concentration of about 1:5000 (volume/volume). The signal was detected using a HRP-conjugated goat anti-rabbit secondary antibody. The HRP-conjugated goat anti-rabbit was diluted with PBS with a concentration of about 1:70000 (volume/volume).

In FIG. 4B, lanes 1 and 3 are insoluble chimeric peptide with flexible linkers. Lane 2 is a soluble chimeric peptide with flexible linkers. Lanes 4 and 5 are purified soluble chimeric peptide with flexible linkers. Lane 6 is a soluble BL21 (DE3) control group. Lane 7 is an insoluble BL21 (DE3) control group. The western blot analysis of the chimeric peptide with flexible linkers revealed protein bands 402 and 403 of the chimeric peptide with flexible linkers. As shown in FIGS. 4A and 4B, under the optimized condition, the expression level of the chimeric peptide with flexible linkers is higher than the expression level of the chimeric peptide with helical linkers.

Example 2

In-Vivo Studies of the Chimeric Peptide

In this second example, immunization efficiency of the chimeric peptide was evaluated by conducting in-vivo studies. The in-vivo studies included an antibody assay and a cytokine assay in mice. In order to perform the antibody assay, two test groups and two control groups were designed, each group including six male BALB/c mice between 6 and 8 weeks old. After production of the chimeric peptide, the chimeric peptide was purified using immobilized metal ion affinity chromatography (IMAC). A chimeric peptide solution was then prepared by dialyzing the chimeric peptide against a physiologic buffer, in this case a phosphate-buffered saline (PBS) solution.

The test groups were treated with the chimeric peptide solution via subcutaneous (SC) and nasal injection. The vaccine dosage of the chimeric peptide solution was about 10 µg of the chimeric peptide. Moreover, the control groups were treated with a PBS solution and a purified Trx-tag solution via subcutaneous (SC) injection.

As discussed with respect to EXAMPLE 1, the chimeric peptide with the flexible linkers had a higher expression than the chimeric peptide with the helical linkers in the host organism. Therefore, the chimeric peptide with the flexible linkers was selected for the in-vivo studies. Moreover, administration of the chimeric peptide solution, the PBS solution, and the purified Trx-tag solution was performed at the baseline, 14th day, and 28th day of the in-vivo study.

In order to evaluate the antibody assay, two weeks after the last injection blood sampling from animal eyes was performed and blood serum was collected and stored at −70° C. In addition, nose lavage of each mouse was collected from the nasal cavity and stored at −70° C. until performing the antibody assay. Assaying the immunoglobulin G (IgG), immunoglobulin G1 (IgG1), immunoglobulin G2a (IgG2a), and immunoglobulin A (IgA) antibodies was performed utilizing an enzyme-linked immunosorbent assay (ELISA).

Figure 5A:
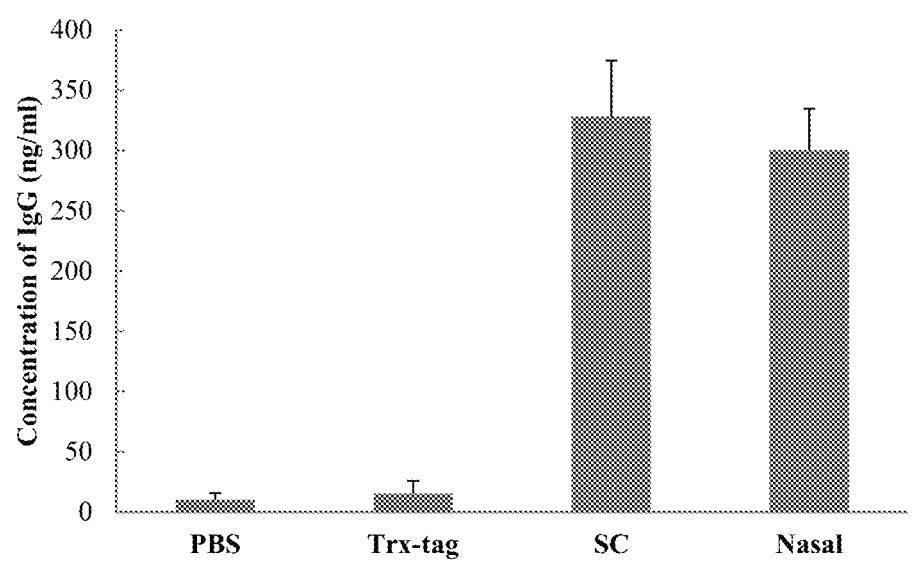
FIG. 5A illustrates immunoglobulin G (IgG) antibody levels in control groups and test groups, according to an implementation of the present disclosure.
Figure 5B:
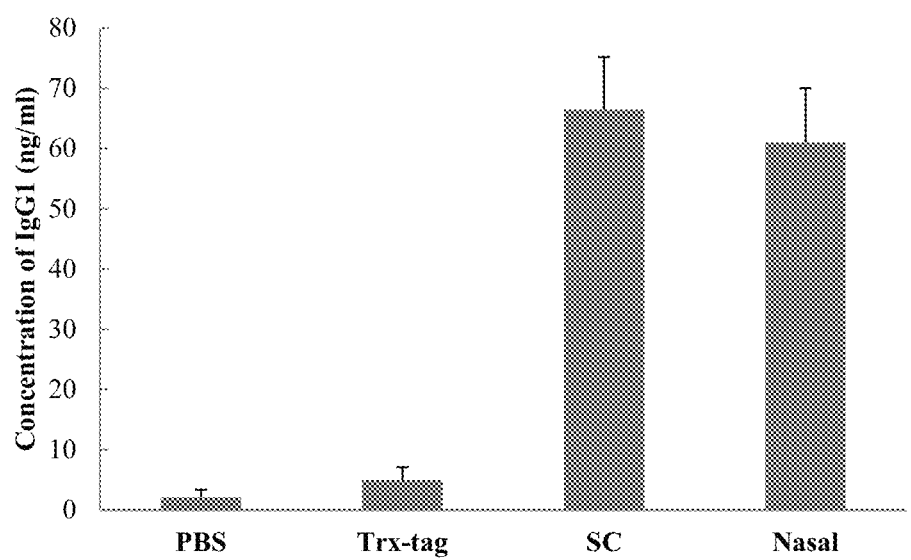
FIG. 5B illustrates immunoglobulin G1 (IgG1) antibody levels in control groups and test groups, according to an implementation of the present disclosure.
Figure 5C:
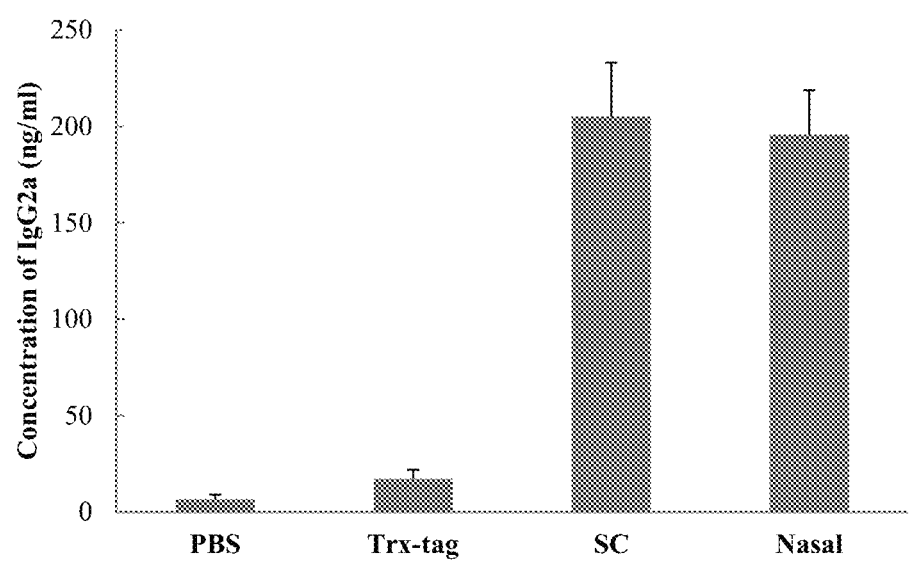
FIG. 5C illustrates immunoglobulin G2a (IgG2a) antibody levels in control groups and test groups, according to an implementation of the present disclosure.
Figure 5D:
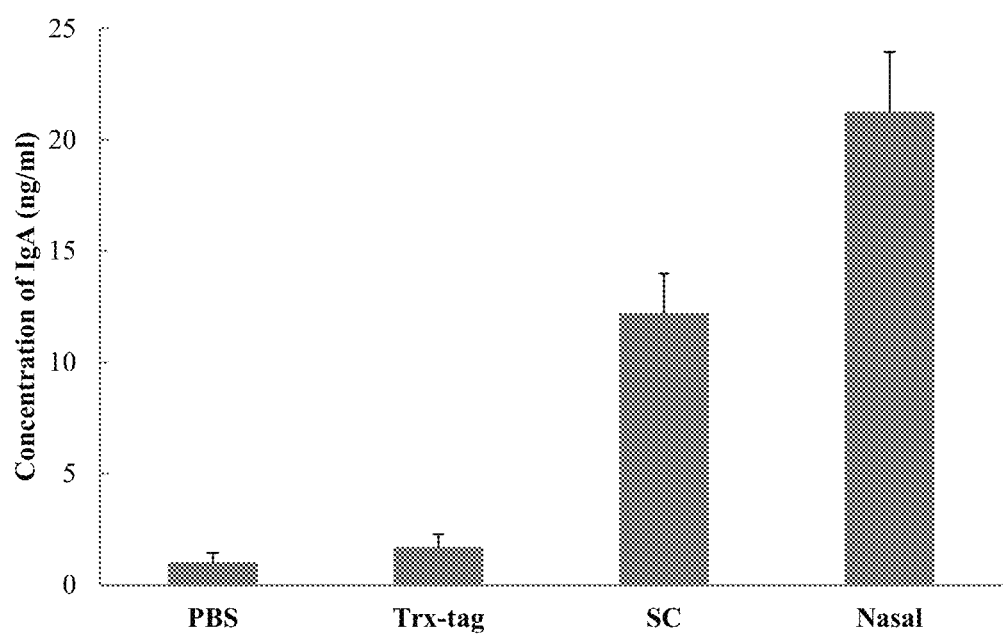
FIG. 5D illustrates immunoglobulin A (IgA) antibody levels in control groups and test groups, according to an implementation of the present disclosure.

The results of these tests are presented in FIGS. 5A-5D. FIG. 5A illustrates an implementation of IgG antibody levels in the control groups and the test groups. FIG. 5B illustrates an implementation of IgG1 antibody levels in the control groups and the test groups. FIG. 5C illustrates an implementation of IgG2a antibody levels in the control groups and the test groups. FIG. 5D illustrates an implementation of IgA antibody levels in the control groups and the test groups.

As shown in FIGS. 5A, 5B, 5C, and 5D, results of the antibody assay demonstrated that the presence of all studied antibodies was significantly higher in the test groups, which were vaccinated with the chimeric peptide, relative to the control groups (p value <0.05). The high titer of these antibodies indicates the better presentation of the chimeric peptide as antigen to antigen-presenting cells (APCs), which leads to a severe immune response.

Furthermore, referring to FIG. 5D, the level of IgA in the test groups, which was treated with the chimeric peptide solution via nasal route, was significantly higher than SC injection (p<0.05). The high titer of IgA was the result of suppressing rapid antigen removal due to localization of antigen in target sites. Moreover, the nasal group which had a higher titer of IgA antibodies induced a higher mucosal immune response.

In order to perform the cytokine assay, the spleen of each mouse in the test groups andthe control groups was removed aseptically and teased to separate the lymphocyte cells. Each group had six male BALB/c mice between 6 and 8 weeks old. After isolation of the lymphocyte cells of the spleens, the number of lymphocyte cells was counted.

The lymphocyte cells of the test groups and the control groups were incubated with a complete medium, which included the chimeric peptide solution, in a cell culture incubator for about 48 hours to induce the production of cytokines. The complete medium included Roswell Park Memorial Institute (RPMI 1640) medium, 10% of heat inactivated fetal bovine serum (FBS), 1% of penicillin/streptomycin antibiotics, 2.5 µg/ml of the plasmocin, and the chimeric peptide solution at a concentration between about 5 µg/ml and about 10 µg/ml.

The lymphocyte cells of the test groups and the control groups as a positive control were incubated with a medium which included phytohemagglutinin with a cell culture incubator to induce the production of cytokine cells for about 48 hours. The complete medium included RPMI 1640 medium, 10% of heat inactivated FBS, 1% of penicillin/streptomycin antibiotics, 2.5 µg/ml of plasmocin, and 3% of phytohemagglutinin (PHA).

Finally, after 48 hours of incubation, the supernatant was collected from the cell culture and stored at −70° C. until performing the cytokine assay. Assaying the interferon gamma (IFN-γ), interleukin 10 (IL-10), and interleukin 4 (IL-4) cytokines were performed by enzyme-linked immunosorbent assay (ELISA).

Figure 6A:
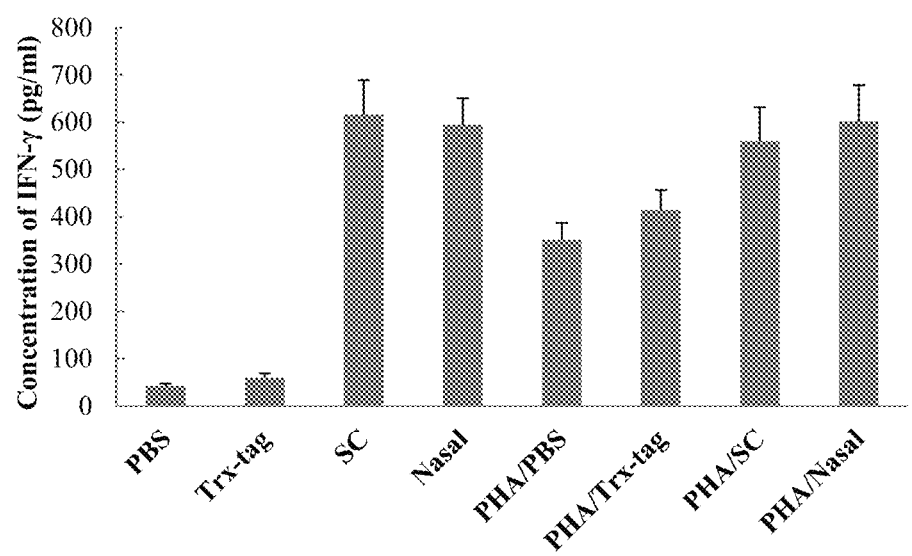
FIG. 6A illustrates interferon gamma (IFN-γ) cytokine levels in control groups and test groups, according to an implementation of the present disclosure.

FIG. 6A illustrates an implementation of IFN-γ cytokine levels in the control groups and the test groups. As shown in FIG. 6A, the levels of IFN-γ in the test groups, which were treated with the chimeric peptide solution through SC and the nasal routes, were higher than the control groups. Moreover, the immune response level of IFN-γ was high in both test groups, about 600 pg/ml, and there was no significant difference between levels of IFN-γ in the test groups with nasal administration and SC injection (p>0.05). Therefore, both test groups with SC and nasal injection had a high potential for inducing IFN-γ cytokine.

Figure 6B:
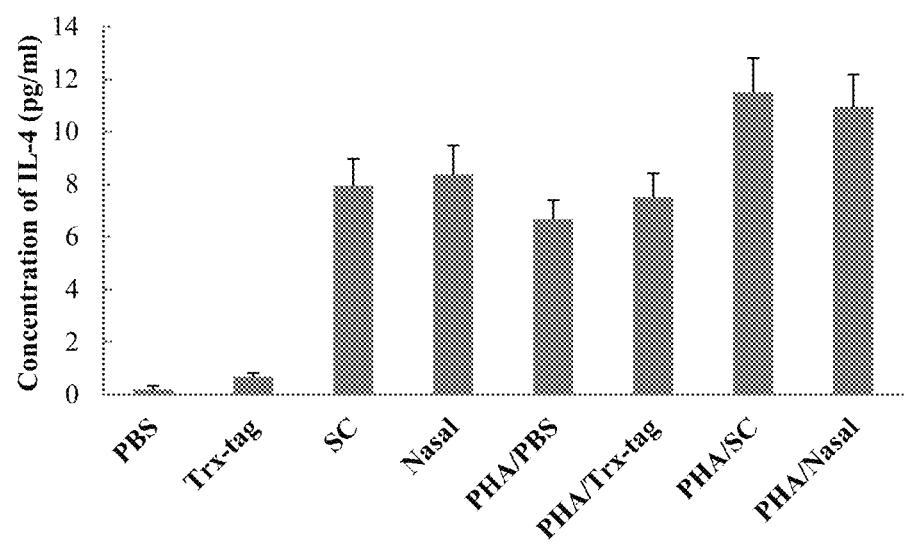
FIG. 6B illustrates interleukin 4 (IL-4) cytokine levels in control groups and test groups, according to an implementation of the present disclosure.

FIG. 6B illustrates an implementation of IL-4 cytokine levels in control groups and test groups. As shown in FIG. 6B, the immune response level of IL-4 in the test groups, which were treated with the chimeric peptide solution through SC and the nasal routes, were higher than the control groups. Moreover, the immune response level of IL-4 was low in both test groups, less than 8.5 pg/ml, and there was no significant difference between the levels of IL-4 in the test groups with nasal administration and SC injection (p>0.05).

Figure 6C:
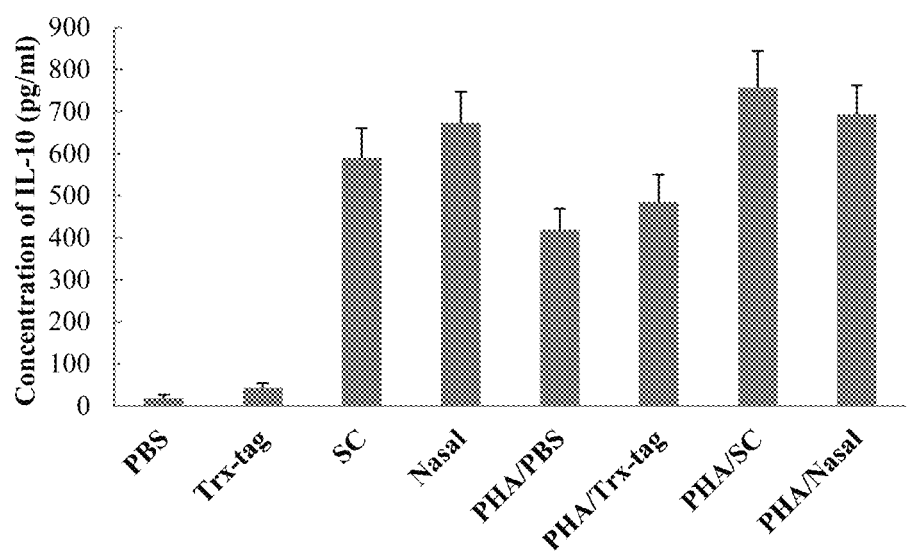
FIG. 6C illustrates interleukin 10 (IL-10) cytokine levels in control groups and test groups, according to an implementation of the present disclosure.

FIG. 6C illustrates an implementation of IL-10 cytokine levels in control groups and test groups. As shown in FIG. 6C, the level of IL-10 response in the test groups, which were treated with the chimeric peptide solution through SC and the nasal routes, were higher than the control groups. Moreover, the level of IL-10 response was 0.59 and 0.67 ng/ml for SC and nasal administration, respectively. Therefore, there was no significant difference in the levels of IL-10 in the test groups with nasal administration and SC injection (p>0.05).

Thus, as shown in FIGS. 6A, 6B, and 6C, it can be seen that the results of the cytokine assays demonstrated that the presence of all studied cytokines was significantly higher in the test groups which were treated with the chimeric peptide than the control groups (p<0.05).

Generally, it is understood that IFN-γ cytokine is produced from T-helper 1 cells (Th1) which are CD4+. The Th1 cells activate macrophages and are responsible for cell-mediated immunity and phagocyte-dependent protective responses. By contrast, T-helper2 (Th2) cells produce IL-4 and IL-10, which are responsible for strong antibody production, eosinophil activation, and inhibition of several macrophage functions. Moreover, Th2 cells mediate the activation and maintenance of the humoral, or antibody-mediated, immune response against extracellular parasites, bacteria, allergens, and toxins.

Referring again to FIGS. 6A, 6B, and 6C, the results of the cytokine assay indicated that treating the chimeric peptide solution in the test groups induces polarized Th1 and Th2 immune responses. Polarized Th1 and Th2 responses are responsible for different types of immune-pathological reactions.

A low concentration of IL-10, for example less than 2 ng/ml, generally has no effect on IFN-γ production, but a high concentration of IL-10, for example 100 ng/ml, decreases the production of IFN-γ production in HTLV-1-infected individuals. As a result, the IL-10 cytokine in high concentrations can modulate the production of IFN-γ cytokine. Therefore, cytokines of both Th1 and Th2 cells are elevated in HTLV-1 infection, and a polarized immune response of Th1 and Th2 cells, specially Th1 cells, is induced against HTLV-1 in this study. With this context, it can be understood that these in-vivo studies confirmed that the administration of chimeric peptide, which was constructed with Tax, gp21, gp46, and gag immunogenic epitopes of HTLV-1, via SC and nasal routes, can stimulate the protective immune response mediated by Th1 and Th2 cells.

In order to induce an effective immune response against HTLV-1, the immune system should be able to activate cellular and humoral immunity in a polarized immune response. As has been presented herein, the chimeric peptide can induce a polarized immune response against HTLV-1 which is mediated by Th1 and Th2. Therefore, the chimeric peptide can be employed to stimulate the immune system, inducing effective immune responses as well as providing immunization against HTLV-1.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for inducing an immune response against human T-lymphotropic virus type 1 (HTLV-1), the method comprising:
   preparing a DNA sequence, the DNA sequence encoding a chimeric peptide with immunogenic epitopes, the immunogenic epitopes including a HTLV-1 Tax epitope, a HTLV-1 gp21 epitope, a HTLV-1 gp46 epitope, and a HTLV-1 gag epitope, the chimeric peptide comprising SEQ ID No. 2 or SEQ ID No. 4;
   producing the chimeric peptide using the DNA sequence;
   forming a purified chimeric peptide by purifying the produced chimeric peptide; and
   inducing an immune response against HTLV-1 using the purified chimeric peptide.

2. The method according to claim 1, wherein the DNA sequence corresponding to the chimeric peptide comprises SEQ ID No. 1 or SEQ ID No. 3.

3. The method according to claim 1, wherein preparing the DNA sequence comprises:
   designing the DNA sequence; and
   synthesizing the designed DNA sequence.

4. The method according to claim 1, wherein producing the chimeric peptide using the DNA sequence comprises:
   preparing a recombinant vector including the DNA sequence;
   obtaining a plurality of recombinant vectors by amplifying the recombinant vector; and
   expressing the chimeric peptide by cloning of the plurality of recombinant vectors in a host organism.

5. The method according to claim 1, wherein purifying the produced chimeric peptide comprises using a chromatographic technique including at least one of affinity chromatography, immobilized metal ion affinity chromatography (IMAC), ion exchange chromatography (IEXC), gel filtration chromatography, and hydrophobic interaction chromatography (HIC).

6. The method according to claim 1, wherein inducing an immune response against HTLV-1 comprises administering the purified chimeric peptide to a person through at least one of a subcutaneous injection (SC), a nasal route, intramuscular injection (IM), and intravenous route (IV).

7. The method according to claim 1, wherein inducing an immune response against HTLV-1 further comprises administering the purified chimeric peptide at an amount between 10 pg and 30 pg.

8. A method for inducing an immune response against human T-lymphotropic virus type 1 (HTLV-1), the method comprising:
   preparing a DNA sequence, the DNA sequence encoding a chimeric peptide with immunogenic epitopes, the immunogenic epitopes including a HTLV-1 Tax epitope, a HTLV-1 gp21 epitope, a HTLV-1 gp46 epitope, and a HTLV-1 gag epitope, the DNA sequence comprising SEQ ID No. 1 or SEQ ID No. 3;
   producing the chimeric peptide using the DNA sequence;
   forming a purified chimeric peptide by purifying the produced chimeric peptide; and
   inducing an immune response against HTLV-1 using the purified chimeric peptide.

9. The method according to claim 8, wherein purifying the produced chimeric peptide comprises purifying the produced chimeric peptide using a chromatographic technique including at least one of affinity chromatography, immobilized metal ion affinity chromatography (IMAC), ion exchange chromatography (IEXC), gel filtration chromatography, and hydrophobic interaction chromatography (HIC).

10. The method according to claim 8, wherein inducing an immune response against HTLV-1 comprises administering the purified chimeric peptide to a person through at least one of a subcutaneous injection (SC), a nasal route, intramuscular injection (IM), and intravenous route (IV).

* * * * *

```
                           SEQUENCE LISTING

<160> NUMBER OF SEQ ID NOS: 6

<210> SEQ ID NO 1
<211> LENGTH: 822
<212> TYPE: DNA
<213> ORGANISM: Artificial
<220> FEATURE:
<223> OTHER INFORMATION: Synthetic

<400> SEQUENCE: 1
aaaaaacagc tgggtgcttt cctgaccaac gttaaaaaac tgctgttcgg ttacccggtt        60
tacgttaaaa aaggtggtgg tggttctggt ggtggtggtt ctggtggtgg tggttctaaa       120
aaaatcgctc agtacgctgc tcagaaccgt cgtggtctgg acctgctgtt ctgggaacag       180
ggtggtctgt gcaaagctct gcaggaacag tgcaaaaaag gtggtggtgg ttctggtggt       240
ggtggttctg tggtggtgg ttctaaaaaa gttgacgctc cgggttacga cccgatctgg       300
ttcctgaaca ccgaaccgtc tcagctgccg ccgaccgctc cgccgctgct gccgcactct       360
aacctggacc acatcctgga accgtctatc ccgtggaaat ctaaactgct gaccctggtt       420
cagctgaccc tgcagtctac caactacacc tgcatcgttt gcatcgaccg tgcttctctg       480
tctacctggc acgttctgta ctcgccaaac gtgagcgttc cgtcttcttc ttctacccg       540 ctgctgtacc cgtctctggc tctgccggct ccgcacctga ccctgccgtt caactggacc       600
cactgcttcg acccgcagat ccaggctatc gtttcttctc cgtgccacaa ctctctgatc       660
ctgccgccgt tctctctgtc tccggttccg accctgggtg gtggtggttc tggtggtggt       720
ggttctggtg gtggtggttc tttcttccgt aaaaaatctc cgacccacga cccgccggac       780
tctgacccgc agatcccgcc gccgtacgtt gaaccgaaaa aa                          822

<210> SEQ ID NO 2
<211> LENGTH: 274
<212> TYPE: PRT
<213> ORGANISM: Artificial
<220> FEATURE:
<223> OTHER INFORMATION: Synthetic
<220> FEATURE:
<221> NAME/KEY: Tax epitope
<222> LOCATION: (3)..(11)
<220> FEATURE:
<221> NAME/KEY: Tax epitope
<222> LOCATION: (14)..(22)
<220> FEATURE:
<221> NAME/KEY: Flexible linker
<222> LOCATION: (25)..(39)
<220> FEATURE:
<221> NAME/KEY: gp21 epitope
<222> LOCATION: (42)..(71)
```

<220> FEATURE:
<221> NAME/KEY: Flexible linker
<222> LOCATION: (74)..(88)
<220> FEATURE:
<221> NAME/KEY: gp46 epitope
<222> LOCATION: (91)..(232)
<220> FEATURE:
<221> NAME/KEY: Flexible linker
<222> LOCATION: (233)..(247)
<220> FEATURE:
<221> NAME/KEY: p19 epitope
<222> LOCATION: (253)..(272)

<400> SEQUENCE: 2

Lys Lys Gln Leu Gly Ala Phe Leu Thr Asn Val Lys Lys Leu Leu Phe
1               5                   10                  15

Gly Tyr Pro Val Tyr Val Lys Lys Gly Gly Gly Ser Gly Gly Gly
            20                  25                  30

Gly Ser Gly Gly Gly Ser Lys Lys Ile Ala Gln Tyr Ala Ala Gln
        35                  40                  45

Asn Arg Arg Gly Leu Asp Leu Leu Phe Trp Glu Gln Gly Gly Leu Cys
50                      55                  60

Lys Ala Leu Gln Glu Gln Cys Lys Lys Gly Gly Gly Ser Gly Gly
65                  70                  75                  80

Gly Gly Ser Gly Gly Gly Ser Lys Lys Val Asp Ala Pro Gly Tyr
            85                  90                  95

Asp Pro Ile Trp Phe Leu Asn Thr Glu Pro Ser Gln Leu Pro Pro Thr
                100                 105                 110

Ala Pro Pro Leu Leu Pro His Ser Asn Leu Asp His Ile Leu Glu Pro
            115                 120                 125

Ser Ile Pro Trp Lys Ser Lys Leu Leu Thr Leu Val Gln Leu Thr Leu
130                 135                 140

Gln Ser Thr Asn Tyr Thr Cys Ile Val Cys Ile Asp Arg Ala Ser Leu
145                 150                 155                 160

Ser Thr Trp His Val Leu Tyr Ser Pro Asn Val Ser Val Pro Ser Ser
                165                 170                 175

Ser Ser Thr Pro Leu Leu Tyr Pro Ser Leu Ala Leu Pro Ala Pro His
            180                 185                 190

Leu Thr Leu Pro Phe Asn Trp Thr His Cys Phe Asp Pro Gln Ile Gln
        195                 200                 205

Ala Ile Val Ser Ser Pro Cys His Asn Ser Leu Ile Leu Pro Pro Phe
210                 215                 220

Ser Leu Ser Pro Val Pro Thr Leu Gly Gly Gly Ser Gly Gly Gly
225                 230                 235                 240

Gly Ser Gly Gly Gly Gly Ser Phe Phe Arg Lys Lys Ser Pro Thr His
            245                 250                 255

Asp Pro Pro Asp Ser Asp Pro Gln Ile Pro Pro Tyr Val Glu Pro
            260                 265                 270

Lys Lys

<210> SEQ ID NO 3
<211> LENGTH: 951
<212> TYPE: DNA
<213> ORGANISM: Artificial
<220> FEATURE:
<223> OTHER INFORMATION: Synthetic

<400> SEQUENCE: 3
aaaaaacagc tgggtgcttt cctgaccaac gttaaaaaac tgctgttcgg ttacccggtt    60

```
tacgttaaaa aactggctga agctgctgct aaagaagctg ctgctaaaga agctgctgct    120
aaagaagctg ctgctaaaga agctgctgct aaagctgctc taaaaaaat cgctcagtac     180 gctgctcaga accgtcgtgg tctggacctg ctgttctggg aacagggtgg tctgtgcaaa    240
gctctgcagg aacagtgcaa aaaactggct gaagctgctc taaagaagc tgctgctaaa     300 gaagctgctg ctaaagaagc tgctgctaaa gaagctgctg ctaaagctgc tgctgttgac    360
gctccgggtt acgacccgat ctggttcctg aacaccgaac cgtctcagct gccgccgacc    420
gctccgccgc tgctgccgca ctctaacctg gaccacatcc tggaaccgtc tatcccgtgg    480
aaatctaaac tgctgaccct ggttcagctg accctgcagt ctaccaacta cacctgcatc    540
gtttgcatcg accgtgcttc tctgtctacc tggcacgttc tgtactcgcc aaacgtgagc    600
gttccgtctt cttcttctac cccgctgctg tacccgtctc tggctctgcc ggctccgcac    660
ctgaccctgc cgttcaactg gacccactgc ttcgaccgc agatccaggc tatcgtttct      720
tctccgtgcc acaactctct gatcctgccg ccgttctctc tgtctccggt tccgaccctg    780
ctggctgaag ctgctgctaa agaagctgct gctaaagaag ctgctgctaa agaagctgct    840
gctaaagaag ccgctgcaaa agctgctgcg ttcttccgta aaaagtctcc gacccacgac    900
ccgccggact ctgacccgca gatcccgccg ccgtacgttg aaccgaaaaa a             951

<210> SEQ ID NO 4
<211> LENGTH: 317
<212> TYPE: PRT
<213> ORGANISM: Artificial
<220> FEATURE:
<223> OTHER INFORMATION: Synthetic
<220> FEATURE:
<221> NAME/KEY: Tax epitope
<222> LOCATION: (3)..(11)
<220> FEATURE:
<221> NAME/KEY: Tax epitope
<222> LOCATION: (14)..(22)
<220> FEATURE:
<221> NAME/KEY: Helical linker
<222> LOCATION: (25)..(54)
<220> FEATURE:
<221> NAME/KEY: gp21 epitope
<222> LOCATION: (57)..(86)
<220> FEATURE:
<221> NAME/KEY: Helical linker
<222> LOCATION: (89)..(118)
<220> FEATURE:
<221> NAME/KEY: gp46 epitope
<222> LOCATION: (119)..(260)
<220> FEATURE:
<221> NAME/KEY: Helical linker
<222> LOCATION: (261)..(290)
<220> FEATURE:
<221> NAME/KEY: p19 epitope
<222> LOCATION: (296)..(315)

<400> SEQUENCE: 4

Lys Lys Gln Leu Gly Ala Phe Leu Thr Asn Val Lys Lys Leu Leu Phe
1               5                   10                  15

Gly Tyr Pro Val Tyr Val Lys Lys Leu Ala Glu Ala Ala Ala Lys Glu
                20                  25                  30

Ala Ala Ala Lys Glu Ala Ala Ala Lys Glu Ala Ala Ala Lys Glu Ala
            35                  40                  45

Ala Ala Lys Ala Ala Ala Lys Lys Ile Ala Gln Tyr Ala Ala Gln Asn
        50                  55                  60

Arg Arg Gly Leu Asp Leu Leu Phe Trp Glu Gln Gly Gly Leu Cys Lys
65                  70                  75                  80
```

```
Ala Leu Gln Glu Gln Cys Lys Lys Leu Ala Glu Ala Ala Lys Glu
                85                  90                  95

Ala Ala Ala Lys Glu Ala Ala Lys Glu Ala Ala Lys Glu Ala
            100                 105                 110

Ala Ala Lys Ala Ala Ala Val Asp Ala Pro Gly Tyr Asp Pro Ile Trp
            115                 120                 125

Phe Leu Asn Thr Glu Pro Ser Gln Leu Pro Thr Ala Pro Pro Leu
        130                 135                 140

Leu Pro His Ser Asn Leu Asp His Ile Leu Glu Pro Ser Ile Pro Trp
145                 150                 155                 160

Lys Ser Lys Leu Leu Thr Leu Val Gln Leu Thr Leu Gln Ser Thr Asn
                165                 170                 175

Tyr Thr Cys Ile Val Cys Ile Asp Arg Ala Ser Leu Ser Thr Trp His
            180                 185                 190

Val Leu Tyr Ser Pro Asn Val Ser Val Pro Ser Ser Ser Thr Pro
            195                 200                 205

Leu Leu Tyr Pro Ser Leu Ala Leu Pro Ala Pro His Leu Thr Leu Pro
210                 215                 220

Phe Asn Trp Thr His Cys Phe Asp Pro Gln Ile Gln Ala Ile Val Ser
225                 230                 235                 240

Ser Pro Cys His Asn Ser Leu Ile Leu Pro Pro Phe Ser Leu Ser Pro
            245                 250                 255

Val Pro Thr Leu Leu Ala Glu Ala Ala Lys Glu Ala Ala Lys
            260                 265                 270

Glu Ala Ala Lys Glu Ala Ala Lys Glu Ala Ala Lys Ala
            275                 280                 285

Ala Ala Phe Phe Arg Lys Lys Ser Pro Thr His Asp Pro Pro Asp Ser
            290                 295                 300

Asp Pro Gln Ile Pro Pro Tyr Val Glu Pro Lys Lys
305                 310                 315

<210> SEQ ID NO 5
<211> LENGTH: 45
<212> TYPE: DNA
<213> ORGANISM: Artificial
<220> FEATURE:
<223> OTHER INFORMATION: Synthetic

<400> SEQUENCE: 5
ggtggtggtg gttctggtgg tggtggttct ggtggtggtg gttct              45

<210> SEQ ID NO 6
<211> LENGTH: 90
<212> TYPE: DNA
<213> ORGANISM: Artificial
<220> FEATURE:
<223> OTHER INFORMATION: Synthetic

<400> SEQUENCE: 6
ctggctgaag ctgctgctaa agaagctgct gctaaagaag ctgctgctaa agaagctgct   60
gctaaagaag ctgctgctaa agctgctgct                                   90
```